US009468231B2

(12) United States Patent
Stahnke et al.

(10) Patent No.: US 9,468,231 B2
(45) Date of Patent: Oct. 18, 2016

(54) LACTIC ACID BACTERIA STRAIN AND ITS USE FOR THE PROTECTION OF FOOD PRODUCTS

(71) Applicant: Chr. Hansen A/S, Hørsholm (DK)

(72) Inventors: Louise Heller Stahnke, Virum (DK); Tina Hornbaek, Frederiksberg (DK); Birthe Jelle, Vedbaek (DK)

(73) Assignee: Chr. Hansen A/S, Hoersholm (DK)

( * ) Notice: Subject to any disclaimer, the term of this patent is extended or adjusted under 35 U.S.C. 154(b) by 158 days.

(21) Appl. No.: 14/228,926

(22) Filed: Mar. 28, 2014

(65) Prior Publication Data

US 2014/0213763 A1 Jul. 31, 2014

Related U.S. Application Data

(62) Division of application No. 12/530,974, filed as application No. PCT/EP2008/053157 on Mar. 17, 2008, now Pat. No. 8,697,422.

(30) Foreign Application Priority Data

Mar. 19, 2007 (DK) .................................. 2007 00418
Apr. 25, 2007 (EP) ...................................... 07106931

(51) Int. Cl.
```
C12N 1/20      (2006.01)
A23L 3/3463    (2006.01)
A23B 4/22      (2006.01)
A23C 9/123     (2006.01)
A23C 9/158     (2006.01)
A23C 19/032    (2006.01)
A23C 19/05     (2006.01)
A23C 19/076    (2006.01)
A23J 3/22      (2006.01)
A23L 1/03      (2006.01)
A23L 1/314     (2006.01)
A23L 1/317     (2006.01)
A23L 3/3571    (2006.01)
C07K 14/335    (2006.01)
C12R 1/225     (2006.01)
C12P 21/00     (2006.01)
```

(52) U.S. Cl.
CPC .............. *A23L 3/34635* (2013.01); *A23B 4/22* (2013.01); *A23C 9/1234* (2013.01); *A23C 9/1585* (2013.01); *A23C 19/0323* (2013.01); *A23C 19/05* (2013.01); *A23C 19/076* (2013.01); *A23J 3/225* (2013.01); *A23K 20/147* (2016.05); *A23K 40/20* (2016.05); *A23K 50/42* (2016.05); *A23L 1/0345* (2013.01); *A23L 1/3175* (2013.01); *A23L 1/31472* (2013.01); *A23L 3/3571* (2013.01); *C07K 14/335* (2013.01); *C12P 21/00* (2013.01); *C12R 1/225* (2013.01); *A23Y 2220/00* (2013.01)

(58) Field of Classification Search
None
See application file for complete search history.

(56) References Cited

U.S. PATENT DOCUMENTS 4,886,673 A 12/1989 Hammes
6,855,518 B2 2/2005 Berjeaud et al.

FOREIGN PATENT DOCUMENTS

EP 0 333 056 9/1989
EP 0 640 291 A1 3/1995
EP 1 475 432 A1 11/2004

OTHER PUBLICATIONS

Mataragas et al., "Antagonistic activity of lactic acid bacteria against *Listeria monocytogenes* in sliced cooked cured pork shoulder stored under vacuum or modified atmosphere at 4± 2° C," Food Microbiology, vol. 20, pp. 259-265, 2003.
Vignolo et al., "Control of *Listeria monocytogenes* in ground beef by 'Lactocin 705', a bacteriocin produced by *Lactobacillus casei* CRL 705," International Journal of Food Microbiology, vol. 29, pp. 397-402, 1996.
Benkerroum et al., "Lyophilized preparations of bacteriocinogenic *Lactobacillus curvatus* and *Lactococcus lactis* subsp. *lactis* as potential protective adjuncts to control *Listeria monocytogenes* in dry-fermented sausages," Journal of Applied Microbiology, vol. 98, No. 1, 2005, pp. 56-63.
Castellano et al.,"Inhibition of *Listeria innocua* and *Brochothrix thermosphacta* in vacuum-packaged meat by addition of bacteriocinogenic *Lactobacillus curvatus* CRL705 and its bacteriocins," Letters in Applied Microbiology, vol. 43, No. 2, Aug. 2006, pp. 194-199.
Dicks et al., "Use of bacteriocin-producing starter cultures of *Lactobacillus plantarum* and *Lactobacillus curvatus* in production of ostrich meat salami", Meat Science, 66 (2004) 703-708.
Garver et al., "Purification and Partial Amino Acid Sequence of Curvaticin FS47, a Heat-Stable Bacteriocin Produced by *Lactobacillus curvatus* FS47," Applied and Environmental Microbiology, Jun. 1994, vol. 60, No. 6, pp. 2191-2195.
Herbert et al., "Genome Sequence of the Bacteriocin-Producing *Lactobacillus curvatus* Strain CRL705", Journal of Bacteriology, 2012, 194(2):538-539.
International Search Report PCT/EP2008/053157 dated Jun. 18, 2008.

(Continued)

*Primary Examiner* — Irene Marx
(74) *Attorney, Agent, or Firm* — Foley & Lardner LLP

(57) ABSTRACT

The present invention refers to a strain of *Lactobacillus curvatus* bacteria deposited in the Deutsche Sammlung von Mikroorganismen und Zellkulturen GmBH (DSMZ) under thew accession number DSM 18775, as well as to compositions, cultures and food products comprising thereof. The strain of the invention is useful for preserving food products, especially under refrigerated conditions.

5 Claims, 8 Drawing Sheets

(56) References Cited

OTHER PUBLICATIONS

Mauriello et al.,"Development of polythene films for food packaging activated with an antilisterial bacteriocin from *Lactobacillus curvatus* 32Y," Journal of Applied Microbiology, vol. 97, No. 2, 2004, pp. 314-322.

Non-Final Office Action U.S. Appl. No. 12/530,974 dated Apr. 19, 2012.

Notice of Allowance dated Dec. 5, 2013 issued in connection with U.S. Appl. No. 12/530,974.

Office action dated Mar. 13, 2013 issued in connection with U.S. Appl. No. 12/530,974.

Office action dated Aug. 29, 2012 issued in connection with U.S. Appl. No. 12/530,974.

Sudirman et al.,"Detection and Properties of Curvaticin 13,a Bacteriocin-Like Substance Produced by *Lactobacillus curvatus* SB13," Current Microbiology, New York, NY, vol. 27, No. 1, Jan. 1, 1993, pp. 35-40.

Vermeiren et al., "Evaluation of meat born lactic acid bacteria as protective cultures for the biopreservation of cooked meat products", International Journal of Food Microbiology 96 (2004) 149-164.

Vogel et al.,"The competitive advantage of *Lactobacillus curvatus* LTH 1174 in sausage fermentations is caused by formation of curvacin A," Systematic and Applied Microbiology, vol. 16, No. 3, 1993, pp. 457-462.

Written Opinion dated Sep. 22, 2009 issued in connection with International Application No. PCT/EP2008/053157.

Xiraphi et al., "Purification and characterization of curvaticin L442, a bacteriocin produced by *Lactobacillus curvatus* L442", Antone van Leeuwenhoek, 89:19-26, 2005.

Ghalfi et al., "Bacterion Activity by Lactobacillus curvatus CWBI-B28 To Inactivate Listeria monocytogens in Cold-Smoked Salmon during 4 degrees Celsius Storage", Journal of Food Protection, vol. 69, No. 5, 2006, pp. 1066-1071.

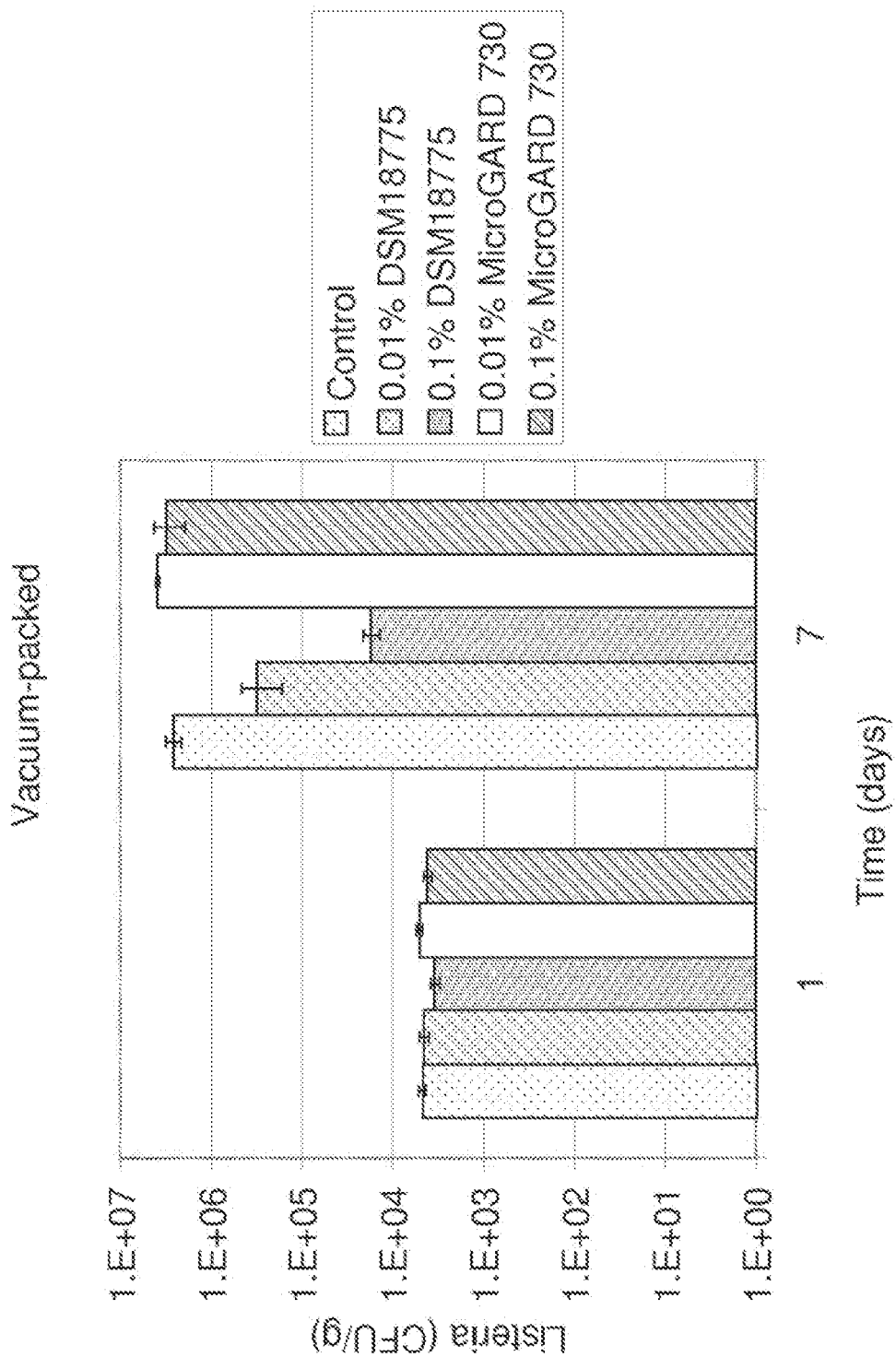

LACTIC ACID BACTERIA STRAIN AND ITS USE FOR THE PROTECTION OF FOOD PRODUCTS

CROSS REFERENCE TO RELATED APPLICATIONS

The present application is a divisional application of U.S. Ser. No. 12/530,974, filed Dec. 1, 2009, granted as U.S. Pat. No. 8,697,422 on Apr. 15, 2014, which is the U.S. National Stage of International Application No. PCT/EP2008/053157, filed on Mar. 17, 2008, which claims the benefit of Danish Patent Application No. PA 2007 00418, filed on Mar. 19, 2007, and European Patent Application No. 07106931.4, filed on Apr. 25, 2007. The entire disclosures of the U.S. and PCT applications are incorporated herein by reference.

The present invention relates to a new lactic acid bacterium that produces protease-sensitive antimicrobial agents (bacteriocins) at low storage temperatures. Particularly, the present invention refers to *Lactobacillus curvatus* DSM 18775, which has been found to be useful for bioprotection of refrigerated products such as Ready-To-Eat (RTE) meat and dairy products.

BACKGROUND ART

Bacterial contamination of food products is known to be responsible for spoilage and for the transmission of food borne illness. This problem is particularly important in RTE meats and dairy products which are not normally reheated by consumers prior to ingestion and which are stored for extended times in refrigerators at 2-10° C. An exemplary case is *Listeria monocytogenes* which is a pathogenic bacterium of particular concern in food products, such as vacuum- or modified atmosphere (MA)-packed RTE meat products, due to its tolerance to refrigeration temperatures, relatively high concentrations of NaCl and anaerobic conditions or in products, such as Fresh Cheese, due to the lack of a heat inactivation step. As a result, a great deal of effort has been expended in attempts to identify natural products that can be safely added to foods for the purpose of inhibiting bacterial growth.

It is well-known to use lactic acid bacteria as starter cultures to induce fermentation of meat products, typically raw salted meat products. The term "starter culture" refers to a preparation containing microbial cells that is intended for inoculating a food matrix to be subjected to fermentation. Starter cultures for meat fermentation are commonly comprised by one or more lactic acid bacteria. The starter culture is intended for providing the desired change in the characteristics of the food matrix during fermentation (e.g. a desired acidification, and certain other sensory and technological parameters). Typically, a starter culture will proliferate during the fermentation process. During the fermentation process the lactic acid bacteria primarily produce lactic acid whereby pH drops to the desired pH-value depending on the culture and the processing conditions (temperature, sugar type/content etc.), and importantly, the sensory properties of the product are distinctly changed.

Antagonistic cultures added to food to inhibit pathogens and/or extend shelf life without changing the sensory properties of the product are termed "protective cultures". In contrast to starter cultures, protective cultures are not intended to change the sensory properties of the product. Their use or that of their metabolic products (organic acids, hydrogen peroxide, enzymes and bacteriocins) is often referred to as "biopreservation" or "bioprotection" (Castel- lano, P. and Vignolo, G., "Inhibition of *Listeria innocua* and *Brochothrix thermrnosphacta* in vacuum-packaged meat by addition of bacteriocinogenic *Lactobacillus curvatus* CRL705 and its bacteriocins", 2006, Letters in Applied Microbiology. Vol. 43: 194-199). This study demonstrates a bacteriostatic effect on a non-patogenic *Listeria* species. No bacteriocidal effect to *Listeria* is reported. Furthermore the "sensoric" evaluation performed was limited to pH measurements.

Besides the establishment of biopreservation as a method to ensure microbiological safety without changing the sensoric characteristics of the product, bioprotective cultures have also been evaluated for their potential of preventing growth of spoilage bacteria (Vermieren, L. et al., "Evaluation of meat born lactic acid bacteria as protective cultures for the biopreservation of cooked meat products", 2004, *International Journal of Food Micro-biology*, 96: 149-164).

The sensory acceptability of cooked meat products treated with bioprotective cultures may limit the use of the preservation method, and the buffering capacity as well as the content of glucose have shown to be key elements to avoid sensory deviations when applying bioprotective cultures (Vermieren et al., *supra*).

A re-growth of *Listeria monocytogenes* has often been observed with the use of bioprotective cultures after an initial phase of inhibition. Re-growth has been ascribed to the development of resistance of *L. monocytogenes* to the bacteriocins, degradation of bacteriocin molecules with endogenous proteases produced during the growth phase, adsorption of the bacteriocins to the surface of the producer strain, or specific interactions with the food matrix (Dicks. L. M. T. et al., "Use of bacteriocin-producing starter cultures of *Lactobacillus plantarum* and *Lactobacillus curvatus* in production of ostrich meat salami", 2004, *Meat Science*, 66: 703-708).

The European patent application EP 1.475.432 discloses two *Lactobacillus curvatus* strains, deposited as PTA-5150 and PTA-5159 and their use for reducing the growth of a microbe in a food or pharmaceutical composition.

The U.S. Pat. No. 4,886,673 discloses three bacteria strains *Lactobacillus curvatus* DSM 4265, *Microccocus varians* DSM4263, and *Debaromyces hansenii* DSM 4260 and their use for preserving meat products. Example 1 describes the use of *Lactobacillus curvatus* DSM 4265 in the production of cut raw sausage.

The European patent application EP 0.640.291 discloses the use of *Lactobacillus curvatus* DSM8430 as a starter culture in salami production. It is specifically mentioned that optimal bacteriocin production occurs at temperatures between 15 and 20° C. and that the activity decreases at low temperatures (+4° C.).

Vogel, R. F. et al., (1993, System. Appl. Microbiol., 16: 457-462) discloses the use of *Lactobacillus curvatus* strain LTH 1174 as a starter culture in salami production. It is specifically mentioned that optimal bacteriocin production occurs at temperatures between 15 and 20° C. and that the activity decreases at low temperatures (+4° C.).

Benkerroum, N. et al. (2005, J. Appl. Microbiol., 98: 56-63) discloses the use of *Lactobacillus curvatus* strain LBPE as a starter culture in the production of dry-fermented sausages. The fermentation is performed at 30° C. and the drying at 14-16° C. No bioprotective effect was demonstrated at low temperatures.

Mauriello, G. et al. (2004, J. Appl. Microbiol., 97: 314-322) discloses the use of polyethylene films for food packing that are treated with partially purified bacteriocin of *Lacto-*

*bacillus curvatus* strain 32Y. In order to produce the bacteriocin this particular strain is grown at 30° C.

SUMMARY OF THE INVENTION

The problem to be solved by the present invention is the provision of a bacteria strain which inhibits the growth of food-borne pathogenic and spoilage bacteria at low temperatures (2-10° C.) without changing the sensory properties of the food product.

The solution is based on a *Lactobacillus curvatus* strain deposited with the accession number DSM 18775.

As it is illustrated below in a non-restricted way, it has been found that the *Lactobacillus curvatus* strain of the present invention is useful for the bioprotection of food products. The strain of the invention can be useful and has proven particularly useful for the inhibition of food-borne pathogenic bacteria and spoilage bacteria owing to the production of bacteriocins.

Food-borne pathogenic and spoilage bacteria can be aerobic, anaerobic or facultative anaerobic, and thus, the elimination of oxygen alone from a food package or from a food storage environment will not effectively eliminate all types of undesired bacteria. More-over, control of the temperature in the storage of food is not totally effective to preclude the growth of such bacteria because several types of pathogenic and spoilage bacteria are able to grow at various temperatures. On the other hand, there are pathogenic bacteria, which due to their tolerance to refrigeration temperatures, relatively high concentrations of NaCl and anaerobic conditions, are of particular concern in RTE food products.

The inventors of the present invention have observed that under refrigeration conditions, the *Lactobacillus curvatus* strain of the invention produces bacteriocins, providing considerable reductions in numbers of food-borne pathogenic bacteria without causing undesirable sensory changes, and also preventing growth of spoilage bacteria in the food product. The fact that the *Lactobacillus curvatus* of the invention is able to produce bacteriocins at a refrigeration temperature implies that said strain can be used for the bioprotection of refrigerated products, and particularly of ready to eat refrigerated products packaged in vacuum or modified atmosphere.

Thus, in one aspect the present invention relates to a strain of *Lactobacillus curvatus* bacterium deposited in the Deutsche Sammlung von Mikroorganismen und Zellkulturen GmBH (DSMZ) under the accession number DSM 18775.

A culture sample of the microorganism was deposited on Sep. 11, 2006 in the Deutsche Sammlung von Mikroorganismen und Zellkulturen GmbH (DSMZ) under the accession number DSM 18775.

In a second aspect the present invention relates to a culture obtained from the strain according to the first aspect of the invention.

An important aspect in the evaluation of the use of a strain as a bioprotective culture is the ability of the strain to work in the food product for which it is intended. In this respect it is not only important that the strain is able to inhibit any undesired food-borne pathogenic bacteria in the product under relevant storage conditions but also that it does not produce any undesired sensory effects (off-taste, off-odors or unwanted color changes). The *Lactobacillus curvatus* strain of the present invention inhibits the food-borne pathogenic bacteria considerably when applied on a wide range of real RTE meat products throughout storage at relevant storage conditions. The inventors have proven by sensory analyses that the culture of the invention does not negatively affect the sensory quality of the food products (such as various RTE meat products) under relevant storage conditions, as it is illustrated below.

Furthermore, in contrast to other strains used as bioprotective cultures, when the culture of the invention is used as a bioprotective culture, no re-growth of *L. monocytogenes* is observed.

Hence, when using a culture according to the present invention there are reduced health risks associated with the ingestion of refrigerated products, due to increased safety of the product during the shelf life. Consequently, the economic loss to the food industry can be considerably reduced.

In a third aspect the present invention relates to a process for preparing a composition inhibiting the growth of at least one food-borne pathogenic bacterium said process comprising: (a) culturing cells of a strain of *Lactobacillus curvatus* according to the first aspect of the invention, which upon culturing in a culture medium, produces a bacteriocin which has inhibitory activity against bacterial strains including *Listeria monocytogenes* to obtain a supernatant comprising the bacteriocin; and (b) separating the supernatant from the cultured cells to obtain the supernatant, thus obtaining a supernatant composition comprising the bacteriocin.

In one embodiment of this aspect the bacteriocin comprising supernatant composition is further subjected to a drying step to obtain a dried culture eluate product. The drying step may conveniently be freeze drying or spray drying. As described in example 8 the process results in a dried culture eluate product which inhibits *Listeria monocytogenes* on meat products packed in a modified atmosphere or in vacuum.

In a further embodiment the growth inhibiting composition have a bacteriocidal effect on at least one food-borne pathogenic bacterium when sufficient amounts are provided. A preferred embodiment is a growth inhibiting composition having a bacteriocidal effect on *Listeria monocytogenes* when provided in sufficient amounts. This is illustrated in example 8 FIG. 7a.

In a fourth aspect the present invention relates to the culture eluate composition resulting from the above-mentioned processes.

In a fifth aspect the present invention relates to the culture medium composition resulting from step (a) of the process of the third aspect of the invention.

In a sixth aspect the present invention relates to the supernatant composition comprising the bacteriocin resulting from step (b) of the process of the third aspect of the invention.

In a seventh aspect the present invention relates to a bacteriocin which has inhibitory activity against bacterial strains including *Listeria monocytogenes* obtainable by the process according to the third aspect of the invention, as well as to cell-free *Lactobacillus curvatus* strain culture-medium-supernatant composition and bactericides comprising said bacteriocin.

In an eighth aspect, the present invention relates to compositions for preserving food products which comprise the *Lactobacillus curvatus* strain according to the first aspect of the invention or the supernatant composition according to the filth aspect of the invention.

In a ninth aspect, the present invention relates to a food product comprising the *Lactobacillus curvatus* strain according to the first aspect of the invention.

In a tenth aspect, the present invention relates to the use of strains and cultures of *Lactobacillus curvatus* according to the first aspect of the invention or the supernatant composition according to the fifth aspect of the invention for preserving food products.

In an eleventh aspect, the present invention relates to the use of strains and cultures of *Lactobacillus curvatus* strain according to the first aspect of the invention or the supernatant composition according to the fifth aspect of the invention, for inhibiting the growth of food-borne pathogenic bacteria on food products preserved in a refrigerated state.

In a twelfth aspect, the present invention relates to the use of strains and cultures of *Lactobacillus curvatus* strain according to the first aspect of the invention or the supernatant composition according to the fifth aspect of the invention, for preventing the growth of spoilage bacteria in food products preserved in a refrigerated state.

In a thirteenth aspect, the present invention relates to a method of preserving food products characterized in that *Lactobacillus curvatus*, according to the first aspect of the invention, is added in an effective amount to said products.

In a fourteenth aspect, the present invention relates to a method for controlling *Listeria* contamination in a food product, on food processing equipment, or on food storage containers, comprising applying the *Lactobacillus* strain with the accession number DSM 18775 to a food product or food processing equipment in an amount sufficient to reduce the amount or prevent growth of *Listeria*.

Throughout the description and claims the word "comprise" and variations of the word, such as "comprising", is not intended to exclude other technical features, additives, components, or steps. Additional objects, advantages and features of the invention will become apparent to those skilled in the art upon examination of the description or may be learned by practice of the invention. The following examples and drawings are provided by way of illustration, and are not intended to be limiting to the present invention.

DETAILED DESCRIPTION OF PARTICULAR EMBODIMENTS

Figure 1:
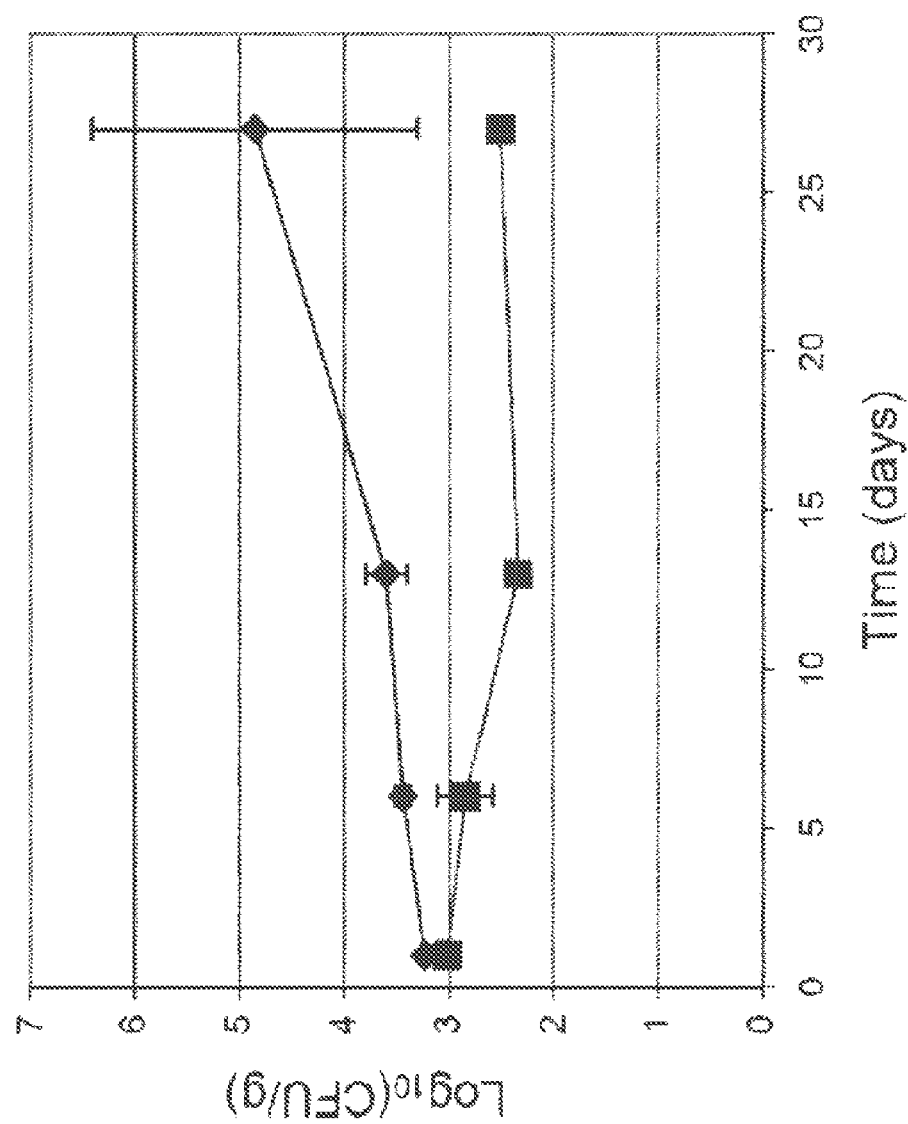
FIG. 1 represents the cell counts of *L. monocytogenes* in slices of Mortadella sausages inoculated with (■) or not inoculated with (♦) DSM 18775 (initial level of $10^7$ CFU/g). The slices of Mortadella sausages were packed in modified atmosphere (30% $CO_2$ and 70% $N_2$) and stored at 7° C. Cell counts were based on determinations made on two different slices of meat, and the bars indicate the standard deviations between these duplicate determinations.

The *Lactobacillus curvatus* strain DMS 18775 of the present invention is a lactic acid bacterium. It was isolated from fermented food and was identified as *Lactobacillus curvatus* by protein gel electrophoresis followed by analyzing and clustering with the reference profiles of the LMG culture collection database. Furthermore, by using an API profile characterization, DMS 18775 was identified as *Lactobacillus curvatus* with 63.4% probability. The strain was characterized by full metabolization of: D-Ribose. D-Galactose, D-Glucose, D-Fructose, D-Mannose, N-Acetylglucosamine, Esculine, D-Maltose and D-Trehalose and partial metabolization of D-Saccharose after 48 h incubation at 30° C. The strain was deposited on Nov. 9, 2006 under the terms of the Budapest treaty at 'Deutsche Sammlung von Microorganismen und Zellkulturen' GmbH (DSMZ). It was assigned de-posit number DSM 18775. The anti-listerial bacteriocin produced by DSM 18775 was determined in an agar well diffusion assay using *Lactobacillus sakei* NCFB 2714 as the indicator organism.

The scope of the present invention also encompasses a strain of *Lactobacillus curvatus* obtained by mutation, variation or recombination of the strain of *Lactobacillus curvatus* DMS 18775, provided that the resulting strain has the ability at a temperature ranging from to 2 to 10° C. of inhibiting the growth of food-borne pathogenic bacteria without causing sensory changes in food.

In the process for preparing the bacteriocin according to the present invention, the strain of the present invention which produces the bacteriocin, is cultured in a medium and under conditions which are favorable for growth, the supernatant is isolated from the resulting culture by separating the supernatant from the cultured cells to obtain a supernatant containing the bacteriocin, and to effect separation, the resulting culture is centrifuged and a supernatant extract containing the bacteriocin is obtained. The supernatant may be concentrated to obtain a concentrate comprising the bacteriocin, and an isolated and purified bacteriocin may be obtained from the supernatant and concentrate and may be dehydrated.

In a particular preferred embodiment of this process the supernatant composition is further subjected to a drying step to obtain a dried culture eluate product. The drying step may conveniently be freeze drying or spray drying, but any drying process which is suitable for drying of bacteriocins, also including vacuum drying and air drying, are contemplated. Although the bacteriocin produced at low temperatures by *Lactobacillus curvatus* DSM 18775 not yet is characterized in details it is known that certain *Lactobacillus curvatus* may produce class II a bacteriocins including Sakacin. Class II a bacteriocins are small heat-stable proteins therefore we expect that even drying methods, which result in moderate heating of the culture eluate product, will result in active compositions.

The bacteriocin according to the present invention is characterized in more detail below with the aid of various microbiological, biochemical and genetic findings which illustrate its properties. The percentages are given by weight. Unit of antibacterial activity is according to the "agar well test". Within the context of the present exposition, inhibitory activity is defined in terms of arbitrary units.

The agar well test is used to determine whether the culture supernatant containing the bacteriocin according to the present invention exhibits inhibitory activity against different strains of spores and bacteria. The inhibition spectrum of the supernatant is thus determined.

The term "food product" as used herein refers to any food that is susceptible to spoilage as a result of bacterial growth and proliferation. Such food products include, but are not limited to, meat, dairy products, vegetables, fruits and grains.

The terms "refrigerated product" or "preserved in a refrigerated state" are equally used and refer to food products which are stored at temperatures ranging from to 2 to 10° C. The food product can be either packaged under vacuum or at modified atmosphere.

As used herein, the term "meat" refers to any meat product or meat by-product (including those processed) from an animal which is consumed by humans or animals, including, without limitation, meat from bovine, ovine, porcine, poultry, fish and crustaceous seafood. As used in the present application, the term "ready to eat meat product", also referred to as RTE meat product, is intended to include any meat product which does not require cooking prior to consumption.

The term "dairy product" is intended to include any food product made using milk or milk products, including, but not limited to, milk, yogurt, ice cream, cheese, butter, and cream.

As used herein the term "shelf life" means the period of time that a food product remains saleable to retail customers. In traditional meat processing, the shelf life of meat and meat by-products is about 30 to 40 days after an animal has been slaughtered. Refrigeration of meat during this period of time is expected to largely arrest and/or retard the growth of pathogenic bacteria, and to a lesser extent, spoilage bacteria. After about 30 to 40 days, however, refrigeration is no longer able to effectively control the proliferation of spoilage bacteria below acceptable levels.

The term "bactericidal effect" as used herein refers to any type of treatment which effect the killing of bacteria (i.e. which reduce their numbers). This is in contrast to a "bacteriostatic effect" which refers to the situation where the treatment only inhibits the growth or reproduction of the bacteria. An agent is said to be a bactericide or a bacteriocide if the agent is able to kill one or more type of bacteria. A bacteriocide is said to possess bacteriocidal or bactericidal activity.

By "bacteriocins" we refer to peptides or protein molecules released extracellularly that are able to kill certain other closely related bacteria by a mechanism by which the producer cell exhibits a degree of specific immunity.

The term "spoilage bacteria" as used herein refers to any type of bacteria that act to spoil food. Spoilage bacteria may grow and proliferate to such a degree that a food product is made unsuitable or undesirable for human or animal consumption. Bacteria are able to proliferate on food surfaces, such as meat surfaces, by assimilating sugars and proteins on such surfaces. By metabolizing these components, spoilage bacteria create by-products including carbon dioxide, methane, nitrogenous compounds, butyric acid, propionic acid, lactic acid, formic acid, sulfur compounds, and other undesired gases and acids. The production of such by-products alter the color of meat surfaces, often turning meat from a red color to a brown, grey or green color. Gaseous by-products generated by spoilage bacteria also give spoiled meat an undesirable odor. The color and odor alterations of meat due to the growth of spoilage bacteria on a the surface of a meat product often make such food product unsaleable to consumers.

In addition to the control of spoilage bacteria, another significant concern in the food processing industry is controlling the growth of food-borne pathogenic bacteria. As used herein, the term "food-borne pathogenic bacteria" refers to any food poisoning organism that is capable of causing disease or illness in animals or humans. The term "food-borne pathogenic bacteria" will be understood to include bacteria that infect the food product (for instance meat) and thereby cause disease or illness, as well as bacteria that produce toxins that cause disease or illness. Preferably, the food-borne pathogenic bacteria is selected from the group: *Aeromonas caviae*; *Aeromonas hydrophila*; *Aeromonas sobria*; *Bacillus cereus*; *Campylobacter jejuni*; *Citrobacter* ssp.; *Clostridium botulinum*; *Clostridium perfringens*; *Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli* O157:H7; *Klebsiella* ssp.; *Listeria monocytogenes*; *Plesiomonas shigelloides*; *Salmonella* ssp.; *Shigella* ssp.: *Staphylococcus aureus*; *Streptococcus* ssp.; *Vibrio cholerae*; *Yersinia enterocolitica*. More preferably, the pathogenic-bacteria are *Listeria monocytogenes*.

As used herein, the expression "effective amount" refers to the amount of *Lactobacillus curvatus* according to the first aspect of the invention which gives rise to an inhibition of the bacterial growth or a reduction of the number of other bacteria from the food product.

The Invention Presented in the Form of Claims

Preferred aspects and embodiments of the invention may be presented in the form of so-called claims. This is given below.

1. A strain of *Lactobacillus curvatus* bacterium deposited in the Deutsche Sammlung von Mikroorganismen und Zellkulturen GmBH (DSMZ) under the accession number DSM 18775.

2. A strain of *Lactobacillus curvatus* according to claim 1 or obtained by mutation, variation or recombination of the strain according to claim 1, characterized in that it has the ability at a temperature ranging from 2 to 10° C. of inhibiting the growth of food-borne pathogenic bacteria without causing sensory changes in food.

3. A culture obtained from the strain according to any of the claims 1 and 2.

4. A composition characterized in that it comprises the *Lactobacillus curvatus* strain according to any of the claims 1 and 2.

5. A composition for preserving food products characterized in that it comprises the *Lactobacillus curvatus* strain according to any of the claims 1 and 2.

6. A composition for preserving food products characterized in that it comprises the *Lactobacillus curvatus* strain according to claim 1.

7. The composition according to any of the claims 5 to 6, for delaying the development of food-borne pathogenic bacteria.

8. The composition according to any of the claims 5 to 7, for delaying the development of spoilage bacteria.

9. The composition according to any of the claims 5 to 8, wherein the food product is packaged under vacuum or at modified atmosphere.

10. The composition according to any of the claims 5 to 9, wherein the food product is RTE meat.

11. The composition according to any of the claims 5 to 10, wherein the food product is a dairy product.

12. A process for preparing a composition having inhibitory activity comprising:
    (a) culturing cells of a strain of *Lactobacillus curvatus* as claimed in any of the claims 1 to 2, which upon culturing in a culture medium, produces a bacteriocin which has inhibitory activity against bacterial strains including *Listeria monocytogenes* to obtain a supernatant comprising the bacteriocin; and
    (b) separating the supernatant from the cultured cells to obtain the supernatant, thus obtaining a supernatant composition comprising the bacteriocin.

13. The process according to claim 12 further comprising isolating the bacteriocin from the supernatant composition to obtain a purified bacteriocin product.

14. The process according to claim 12 further comprising concentrating the supernatant composition to obtain a concentrate comprising the bacteriocin.

15. The culture medium composition resulting from step (a) of the process of claim 12.

16. The supernatant composition comprising the bacteriocin resulting from step (b) of the process of claim 12.

17. A bacteriocin which has inhibitory activity against bacterial strains including *Listeria monocytogenes* obtainable by the process of claims 12 to 14.

18. A cell-free *Lactobacillus curvatus* strain culture-medium-supernatant composition comprising the bacteriocin of claim 17.

19. A bactericide which comprises the bacteriocin as defined in claim 17.

20. A food product comprising the *Lactobacillus curvatus* or a variant or mutant thereof according to any of the claims 1 and 2.

21. A food product comprising the *Lactobacillus curvatus* according to claim 1.

22. The food product according to any of the claims 20 to 21, wherein the food product is packaged under vacuum or at modified atmosphere.

23. The food product according to any of the claims 20 to 22 which is preserved in a refrigerated state and has on its surface a biological barrier consisting of *Lactobacillus curvatus* according to any of the claims 1 and 2.

24. Use of strains and cultures of *Lactobacillus curvatus* according to any of the —claims 1 to 3 or the supernatant composition according to claim 16, for preserving food products.

25. Use of strains and cultures of *Lactobacillus curvatus* according to any of the claims 1 and 3, for preserving food products.

26. Use of strains and cultures of *Lactobacillus curvatus* according to any of the claims 1 to 3 or the supernatant composition according to claim 16, for inhibiting the growth of food-borne pathogenic bacteria on food products preserved in the refrigerated state.

27. Use of strains and cultures of *Lactobacillus curvatus* according to any of the claims 1 to 3 or the supernatant composition according to claim 16, for delaying the appearance of unwanted sensory effects (off-taste, off-odors or unwanted color changes) in food products preserved in the refrigerated state.

28. Use of strains and cultures of *Lactobacillus curvatus* according to any of the claims 1 to 3 or the supernatant composition according to claim 16, for preventing the growth of spoilage bacteria in food products preserved in the refrigerated state.

29. The use according to any of the claims 24 to 28, wherein the food product is packaged under vacuum or at modified atmosphere.

30. The use according to any of the claims 24 to 29, wherein the food product is a RTE meat product.

31. The use according to any of the claims 24 to 29, wherein the food product is a dairy product.

32. The use according to any of the claims 24 to 31, wherein the food-borne pathogenic bacterium is *Listeria monocytogenes*.

33. A process of preserving food products characterized in that *Lactobacillus curvatus* according to any of the claims 1 to 2 or the supernatant composition according to claim 16 is added in an effective amount to said food products.

34. The process according to claim 33, wherein the *Lactobacillus curvatus* strain or the supernatant composition is added during the manufacture process of the food product.

35. The process according to claim 33, wherein the *Lactobacillus curvatus* strain or the supernatant composition is added to the food product so as to form a barrier on the surface of said product.

36. The process according to any of the claims 33 to 35, wherein the food product is a RTE meat.

37. The process according to any of the claims 33 to 35, wherein the food product is a dairy product.

38. A method for controlling *Listeria* contamination in a food product, on food processing equipment, or on food storage containers, comprising applying the *Lactobacillus* strain with the accession number DSM 18775 to a food product or food processing equipment in an amount sufficient to reduce the amount of *Listeria*.

EXAMPLES

Example 1

Strain Identification and Bacteriocin Production

After growth of DSM 18775 in MRS (De Man, Rogosa and Sharpe, Difco, V W R, Herlev, Denmark) broth for 22 h at 25° C., the cell suspension was centrifuged at 4,000×g for 15 min. The supernatant was adjusted to pH 6.0±0.1 with 1N NaOH and filter sterilized (0.45 μm). Two-fold dilutions of the supernatant were made in sterile ion-exchanged water and 50 μl of each bacteriocin dilution were added to wells in MRS agar containing the indicator organism, *Lactobacillus sakei* NCFB 2714, in a concentration of $10^6$ CFU/ml. To verify the proteinaceus nature of the inhibitory substances, a solution of the proteolytic enzyme, Proteinase K, was applied next to one well of the agar well diffusion assay. The bacteriocin activity of the cell supernatant was defined as the reciprocal of the highest dilution causing an inhibition zone in the agar assay. Inhibition zones caused by a proteinaceus compound, bacteriocin, were observed with an activity of 500 units/ml cell supernatant, clearly indicating the ability of DSM 18775 to produce considerable amounts of anti-listerial bacteriocin.

Example 2

Application Trial with *Lactobacillus curvatus* DSM 18775 on Sliced Mortadella-Type Sausage (I)

The anti-listerial effect of DSM 18775 and the sensory Impact of the culture were evaluated on sliced Mortadella sausage. A 5 strain *L. monocytogenes* cocktail was added to the surface of the RTE meat product ($10^3$ CFU/g) followed by inoculation of the bioprotective culture ($10^7$ CFU/g). The product was packed in a modified atmosphere (30% $CO_2$ and 70% $N_2$) and stored at 7° C. for 27 days.

Cell counts of the bioprotective culture were determined by plating appropriate 10-fold dilutions made in peptone saline onto MRS-agar plates and incubating anaerobically for 3 days at 30° C. DSM 18775 proliferated on the product and reached approx. $10^8$ CFU/g after 1 week of storage and approx. $10^9$ CFU/g by the end of storage.

*Listeria* cell counts were determined by plating appropriate 10-fold dilutions made in peptone saline onto *listeria* selective PALCAM agar plates (Oxoid A/S, Glostrup, Denmark) and incubating microaerophilic for 48 h at 37° C. These cell counts can be seen in FIG. 1, showing a bacterlocidal effect of DSM 18775 on *L. monocytogenes*.

Sensory descriptive triangle tests carried out by a panel of 10 judges did not show any significant effect of adding the bioprotective culture upon 11 days of storage. After 21 days of storage (end of shelf life), the products with added bioprotective culture were perceived as fresher in taste and odor compared to the products without DSM 18775 added, which were characterized as more insipid.

Example 3

Application Trial with *Lactobacillus curvatus* DSM 18775 on Sliced Mortadella-Type Sausage (II), Very Finely Chopped The anti-listerial effect of DSM 18775 and the sensory impact of the culture was evaluated on sliced Mortadella sausage made of very finely chopped meat. A 5 strain *L. monocytogenes* cocktail was added to the surface of the RTE meat product ($10^3$ CFU/g) followed by inoculation of the bioprotective culture ($10^7$ CFU/g). The product was packed in a modified atmosphere (30% $CO_2$ and 70% $N_2$) and stored at 7° C. for 27 days.

Cell counts of the bioprotective culture were determined by plating appropriate 10-fold dilutions made in peptone saline onto MRS-agar plates and incubating anaerobically for 3 days at 30° C. DSM 18775 proliferated on the product and reached approx. $10^8$ CFU/g after 1 week of storage and approx. $10^9$ CFU/g by the end of storage.

Figure 2:
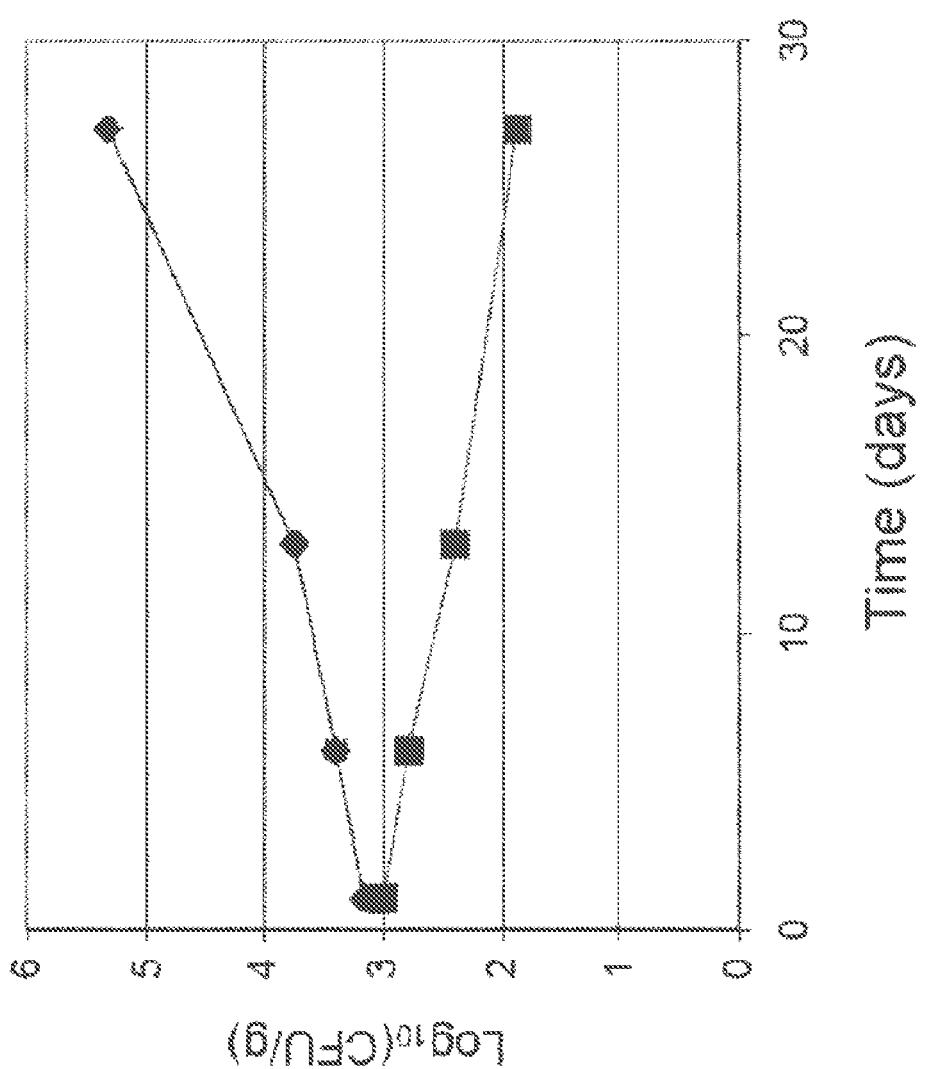
FIG. 2 represents the cell counts of *L. monocytogenes* in slices of Mortadella sausages made of finely chopped meat inoculated with (■) or not inoculated with (♦) DSM 18775 (initial level of $10^7$ CFU/g). The slices of Mortadella sausages were packed in modified atmosphere (30% $CO_2$ and 70% $N_2$) and stored at 7° C. Cell counts were based on determinations made on two different slices of meat, and the bars indicate the standard deviations between these duplicate determinations.

*Listeria* cell counts were determined by plating appropriate 10-fold dilutions made in peptone saline onto *listeria* selective PALCAM agar plates (Oxoid A/S, Greve, Denmark) followed by microaerophilic incubation for 48 h at 37° C. *Listeria* cell counts can be seen in FIG. 2, clearly illustrating a bacteriocidal effect of DSM 18775 on *L. monocytogenes* throughout 27 days of storage.

Sensory descriptive triangle tests carried out by a panel of 10 judges did not show any significant sensory effect of adding the bioprotective culture upon 11 days of storage or at the end of shelf life. i.e. after 21 days of storage.

Example 4

Application Trial with *Lactobacillus curvatus* DSM 18775 on Cooked, Smoked and Sliced Ham The anti-listerial effect of DSM 18775 and the sensory impact of the culture was evaluated on cooked, smoked and sliced ham. A 5 strain *L. monocytogenes* cocktail was added to the surface of the RTE meat product ($10^3$ CFU/g) followed by inoculation of the bioprotective culture ($10^7$ CFU/g). The product was packed in a modified atmosphere (30% $CO_2$ and 70% $N_2$) and stored at 7° C. for 27 days.

Cell counts of the bioprotective culture were determined by plating appropriate 10-fold dilutions made in peptone saline onto MRS-agar plates and incubating anaerobically for 3 days at 30° C. DSM 18775 proliferated on the product and reached approx. $10^8$ CFU/g after 1 week of storage and approx. $5 \times 10^8$ CFU/g by the end of storage.

Figure 3:
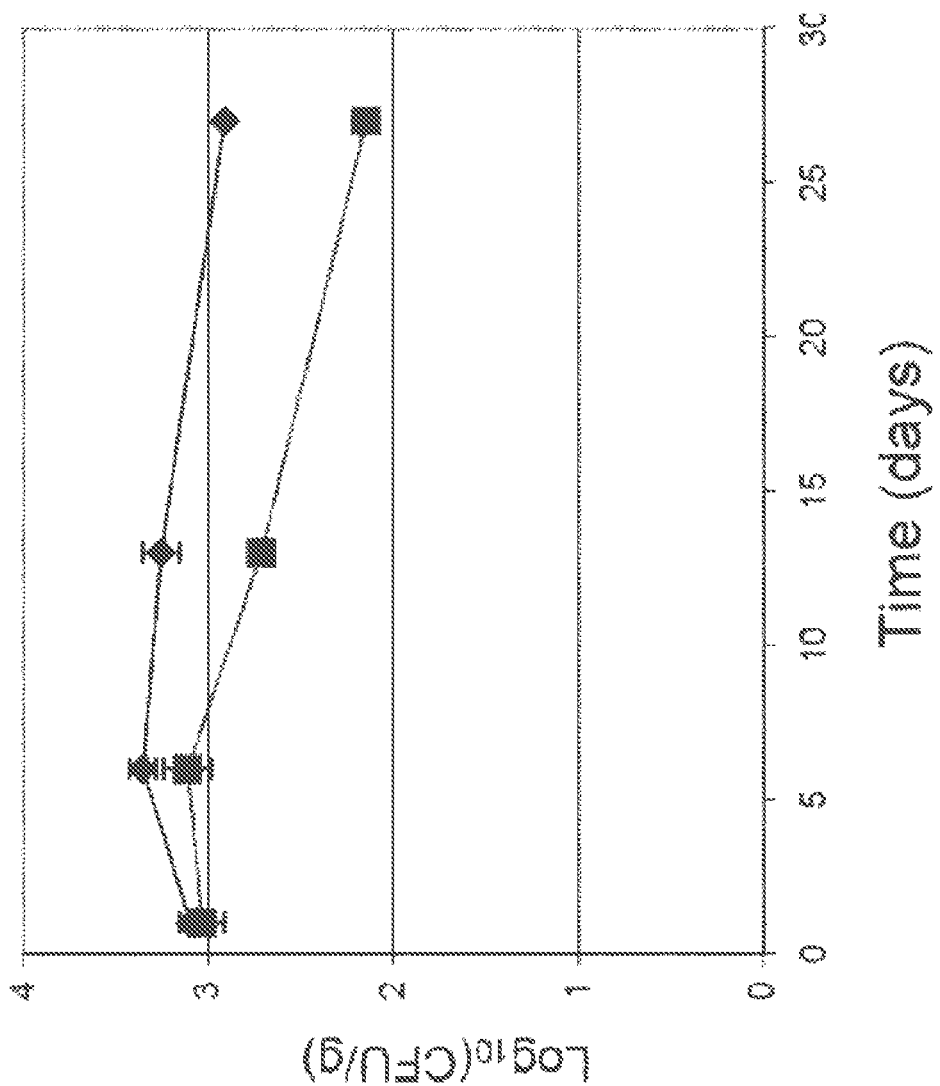
FIG. 3 represents the cell counts of *L. monocytogenes* in slices of cooked, smoked ham, inoculated with (■) or not inoculated with (♦) DSM 18775 (initial level of $10^7$ CFU/g). The ham slices were packed in modified atmosphere (30% $CO_2$ and 70% $N_2$) and stored at 7° C. Cell counts were based on determinations made on two different slices of meat, and the bars indicate the standard deviations between these duplicate determinations.

*Listeria* cell counts were determined by plating appropriate 10-fold dilutions made in peptone saline onto *listeria* selective PALCAM agar plates followed by microaerophilic incubation for 48 h at 37° C. This product did not support growth of *L. monocytogenes* (probably due to the smoking processing step), but larger reductions in cell counts of *L. monocytogenes* throughout 27 days of storage were observed in the presence compared to the absence of DSM 18775 (FIG. 3).

Sensory descriptive triangle test carried out by a panel of 10 judges did not show any significant sensory effect of adding the bioprotective culture upon 11 days of storage or at the end of shelf life, i.e. after 21 days of storage.

Example 5

Application Trial with *Lactobacillus curvatus* DSM 18775 on Wiener Sausages

The anti-listerial effect of DSM 18775 and the sensory impact of the culture were evaluated on Wiener Sausages. A 5 strain *L. monocytogenes* cocktail was added to the surface of the RTE meat product ($10^3$ CFU/g) followed by Inoculation of the bioprotective culture ($10^7$ CFU/g). The sausages were vacuum packed and stored at 7° C. for 27 days.

Cell counts of the bioprotective culture were determined by plating appropriate 10-fold dilutions made in peptone saline onto MRS-agar plates and incubating anaerobically for 3 days at 30° C. DSM 18775 proliferated on the product and reached approx. $10^8$ CFU/g after 1 week of storage and approx. $5 \times 10^8$ CFU/g by the end of storage.

Figure 4:
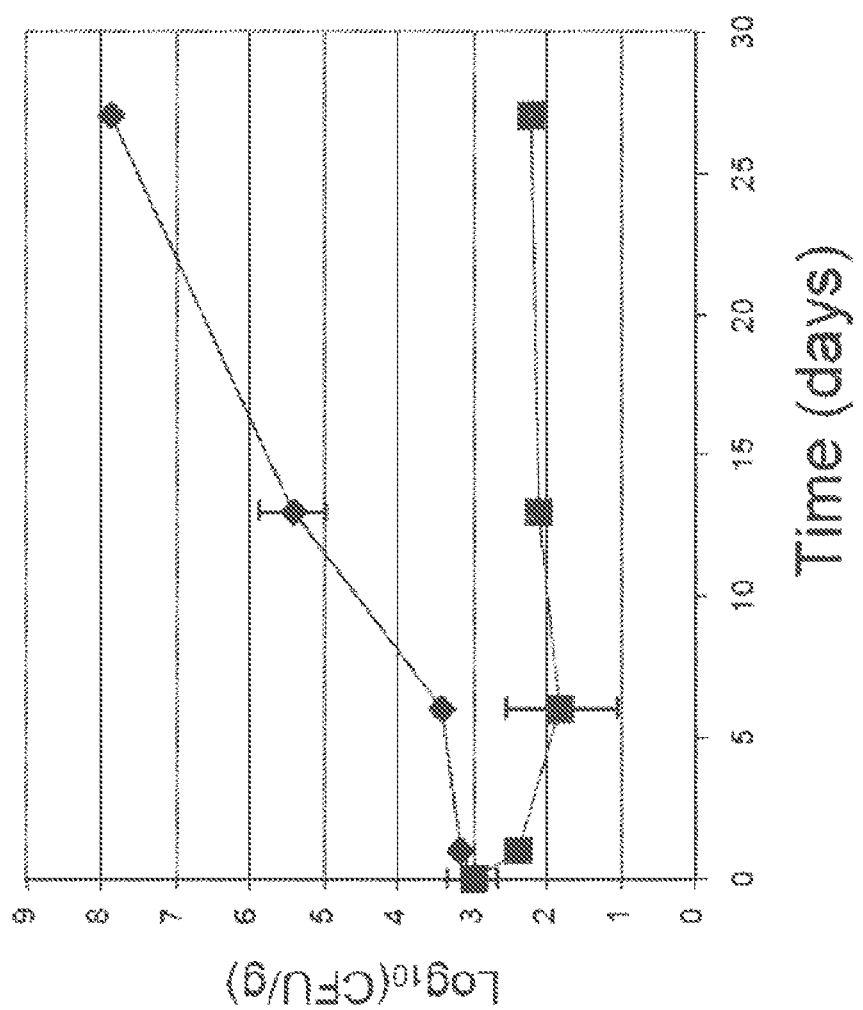
FIG. 4 represents the cell counts of *L. monocytogenes* in Wiener Sausage, inoculated with (■) or not inoculated with (♦) DSM 18775 (initial level of $10^7$ CFU/g). The Wiener Sausages were vacuum-packed and stored at 7° C. Cell counts were based on determinations made on two different sausages, and the bars indicate the standard deviations between these duplicate determinations.

*Listeria* cell counts were determined by plating appropriate 10-fold dilutions made in peptone saline onto *listeria* selective PALCAM agar plates followed by microaerophilic incubation for 48 h at 37° C. An instant bacteriocidal effect of DSM 18775 was found on *L. monocytogenes* and the reduced cell count was constant throughout storage in contrast to the pronounced growth of *L. monocytogenes* found in the absence of bioprotective culture in this RTE meat product (FIG. 4).

An agar well diffusion assay was used to detect bacteriocins produced by DSM 18775 in the Wiener Sausages using *Lactobacillus sakei* as indicator organism. Bacteriocin was extracted from the sausages by homogenizing with 0.02M HCl (1:2, w/v), centrifuging at 16,000×g for 5 min at 5° C., adjusting the supernatant to pH 6.0±0.1 with 1N NaOH and filter sterilizing (0.45 μm). To verify the proteinaceus nature of the inhibitory substances, a solution of the proteolytic enzyme, Proteinase K, was applied next to the sausage extract in the agar well diffusion assay. Inhibition zones caused by a proteinaceus compound, presumably bacteriocin, were observed from extracts derived from Wiener Sausage after 11, 21 and 28 days of storage.

In sensory descriptive triangle tests carried out by a panel of 10 judges Wiener Sausages with added DSM 18775 were evaluated as slightly different, and fresher, than sausages without bioprotective culture after 11 days of storage, whereas no significant effect of DSM 18775 was found on the sensory quality after 21 days of storage. i.e. at the end of shelf life.

Example 6

Application Trial with *Lactobacillus Curvatus* DSM 18775 on Cooked Sliced Ham

The anti-listerial effect of DSM 18775 and the sensory impact of the culture were evaluated on cooked sliced ham. A 5 strain *L. monocytogenes* cocktail was added to the surface of the RTE meat product ($10^3$ CFU/g) with or without the concomitant inoculation of the bioprotective culture ($10^7$ CFU/g). The product was packed in a modified atmosphere (30% $CO_2$ and 70% $N_2$) and stored at 5° C. for 4 weeks.

Cell counts of the bioprotective culture were determined by plating appropriate 10-fold dilutions made in peptone saline onto MRS-agar plates and incubating anaerobically for 3 days at 30° C. DSM 18775 proliferated on the product and reached approx. $10^8$ CFU/g by the end of storage.

Figure 5:
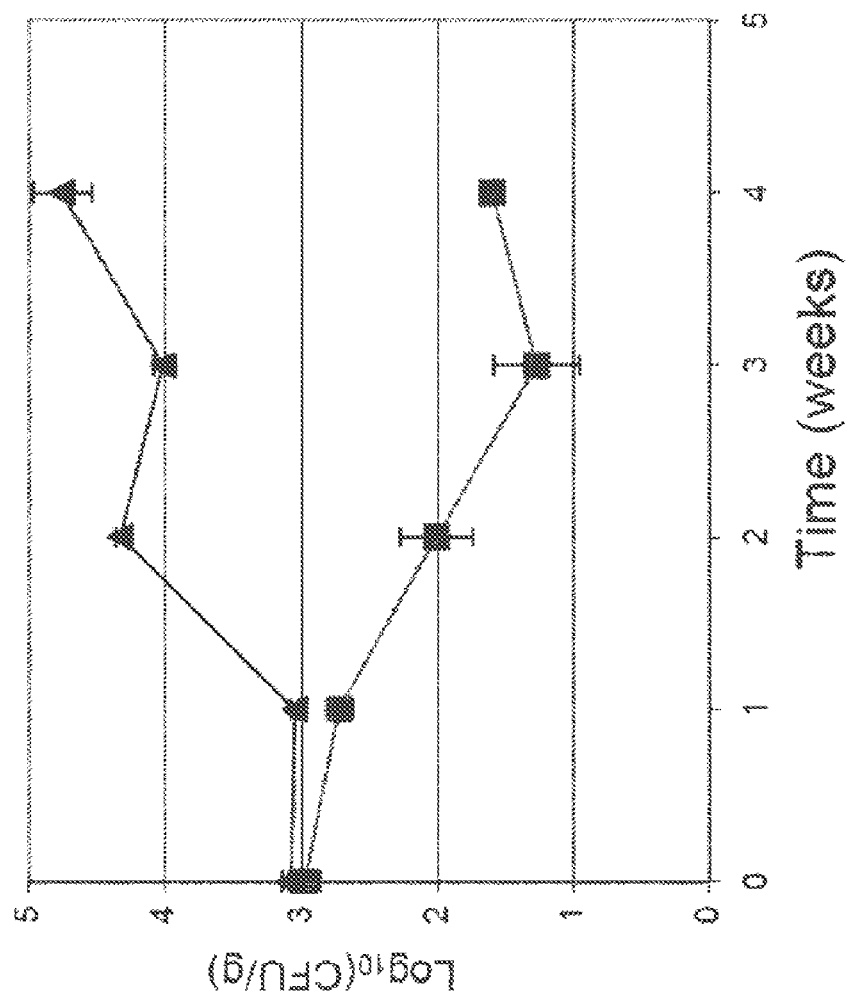
FIG. 5 represents the cell counts of *L. monocytogenes* in slices of cooked ham, inoculated with (■) or not inoculated with (♦) DSM 18775 (initial level of $10^7$ CFU/g). The ham slices were packed in modified atmosphere (30% $CO_2$ and 70% $N_2$) and stored at 5° C. Cell counts were based on determinations made on two different slices of cooked ham, and the bars indicate the standard deviations between these duplicate determinations.
Figure 6:
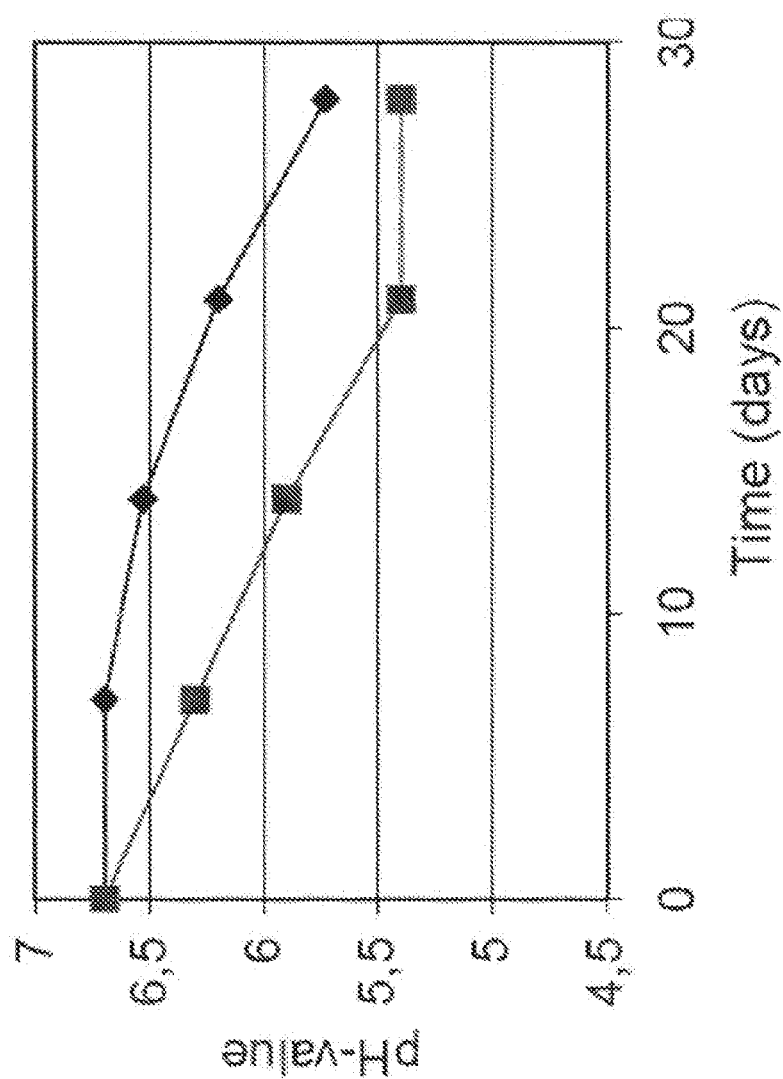
FIG. 6 represents the development in pH in cheeses inoculated with DSM 18775 (■) or not inoculated with DSM 18775 (♦) (initial level of $10^7$ CFU/g). The cheeses were packed in vacuum and stored at 9° C. pH is measured in a suspension of cheese and water (1:1) stirred for 30 min before measurement of pH (using a PHM 92 pH-meter, Radiometer, Copenhagen, DK).

*Listeria* cell counts were determined by plating appropriate 10-fold dilutions made in peptone saline onto *listeria* selective PALCAM agar plates followed by microaerophilic incubation for 48 h at 37° C. A clear bacteriocidal effect of DSM 18775 was found on *L. monocytogenes* as seen in FIG. 6 with 1-2 $\log_{10}$ unit reductions observed throughout storage (FIG. 5).

In sensory descriptive triangle tests carried out by a panel of 8 judges, no significant differences were found in the sensory quality of the products in the presence compared to the absence of bioprotective culture throughout the storage period.

Example 7

Application Trial with *Lactobacillus curvatus* DSM 18775 in Fresh Cheese 20 kg whole milk (pasteurized at 72-73° C. homogenized and standardized to 3.0% of butter fat) were added $3.5 \times 10^{10}$ CFU of the bioprotective culture DSM 18775, corresponding to approx. $10^7$ CFU/g of cheese. At the time of inoculation the temperature of the milk was 35° C. DSM 18775 was pre-ripened in the milk for 30 min at 35° C. before addition of the rennet. The manufacture of the fresh cheese followed a standard protocol for fresh cheese: cutting the curd, heating the curd at 43° C. for 30 min, drainage of 50% whey, dry salting to obtain a final salt content of 2% in the cheese. After manufacture, the cheese was divided into smaller pieces, vacuum packed separately and stored for 4 weeks at 9° C.

Cell counts of the bioprotective culture were determined by plating appropriate 10-fold dilutions made in peptone saline onto MRS-agar plates and incubating anaerobically for 3 days at 30° C. The initial cell count of DSM 18775 was 10-times lower than expected (approx. $10^6$ CFU/g of cheese), but during storage, DSM 18775 proliferated in the cheese and reached approx. $10^8$ CFU/g after 4 weeks.

Throughout storage, a faster reduction of pH was observed in the cheese with the added bioprotective culture, but by the end of storage no significant difference was observed in the cheese with or without the bioprotective culture as seen in FIG. 6.

A trained panel of three assessors evaluated the sensory impact of adding the bioprotective culture to fresh cheese. The cheeses were mainly characterized on taste and texture. The assessment was done at 10° C. The assessors described the cheese with the added DSM 18775 as fresher, more intense, with improved texture, compared to the cheese without the DSM 18775, which was characterized as neutral, tasteless and crumbling.

Bacteriocins produced by DSM 18775 in the Fresh Cheese during storage were determined in an agar well diffusion assay using *Lactobacillus sakei* NCFB 2714 as the indicator organism. Bacteriocin was extracted from the cheese by homogenizing with 0.02M HCL (1:5, w/v), centrifuging at 16,000×g for 5 min at 5° C., adjusting the supernatant to pH 4.5±0.1 with 1N NaOH and filter sterilizing (0.45 μm). To verify the proteinaceus nature of the inhibitory substances, a solution of the proteolytic enzyme, Proteinase K, was applied next to the cheese extract in the agar well diffusion assay.

Bacteriocin was produced and detected in the fresh cheese during storage in increasing amounts during the first 3 weeks (Table 1) and in a concentration range expected to inhibit growth of *L. monocytogenes* in the cheese.

TABLE 1

| Day of analysis during storage | Bacteriocin activity in cheese with added DSM 18775 (unit/mg) | Bacteriocin activity in cheese without added DSM 18775 (unit/mg) |
| --- | --- | --- |
| 0 | — | — |
| 7 | 8 | — |
| 14 | 16 | — |
| 21 | 32 | — |
| 28 | 32 | — |

Example 8

Comparison of *Lactobacillus curvatus* DSM 18775 Culture Eluate with a Commercially Available Culture Eluate The antilisterial effect of freeze dried eluate from DSM18775 was compared to the effect of a similar type of product from Danisco, MicroGARD 730, on sliced emulsion sausages.

A 5-strain cocktail of *Listeria monocytogenes* in final concentrations of approx. 5e03 CFU/g was added to slices of emulsion sausages. Solutions of culture eluates of DSM18775 and MicroGARD 730 dissolved in Milli-Q water and filter sterilized (0.2 mm) were added in final concentrations of 0.01 and 0.1% (w/w). As a control, the same volume of saline peptone instead of culture eluate was added to slices of emulsion sausage. The inoculated slices of emulsion sausages were packed in Modified Atmosphere (MA 30% CO2+70% N2) or vacuum packed and stored at 7° C.

After 1 and 7 days of storage, the MA-packed and vacuum-packed meat were examined for the content of listeria by making appropriate 10-fold dilutions in saline peptone and spread-plating on PALCAM agar plates followed by 2 days of microaerophilic incubation at 30° C. Slices without added listeria were sensory evaluated after 1 and 7 days of storage.

Figure 7A:
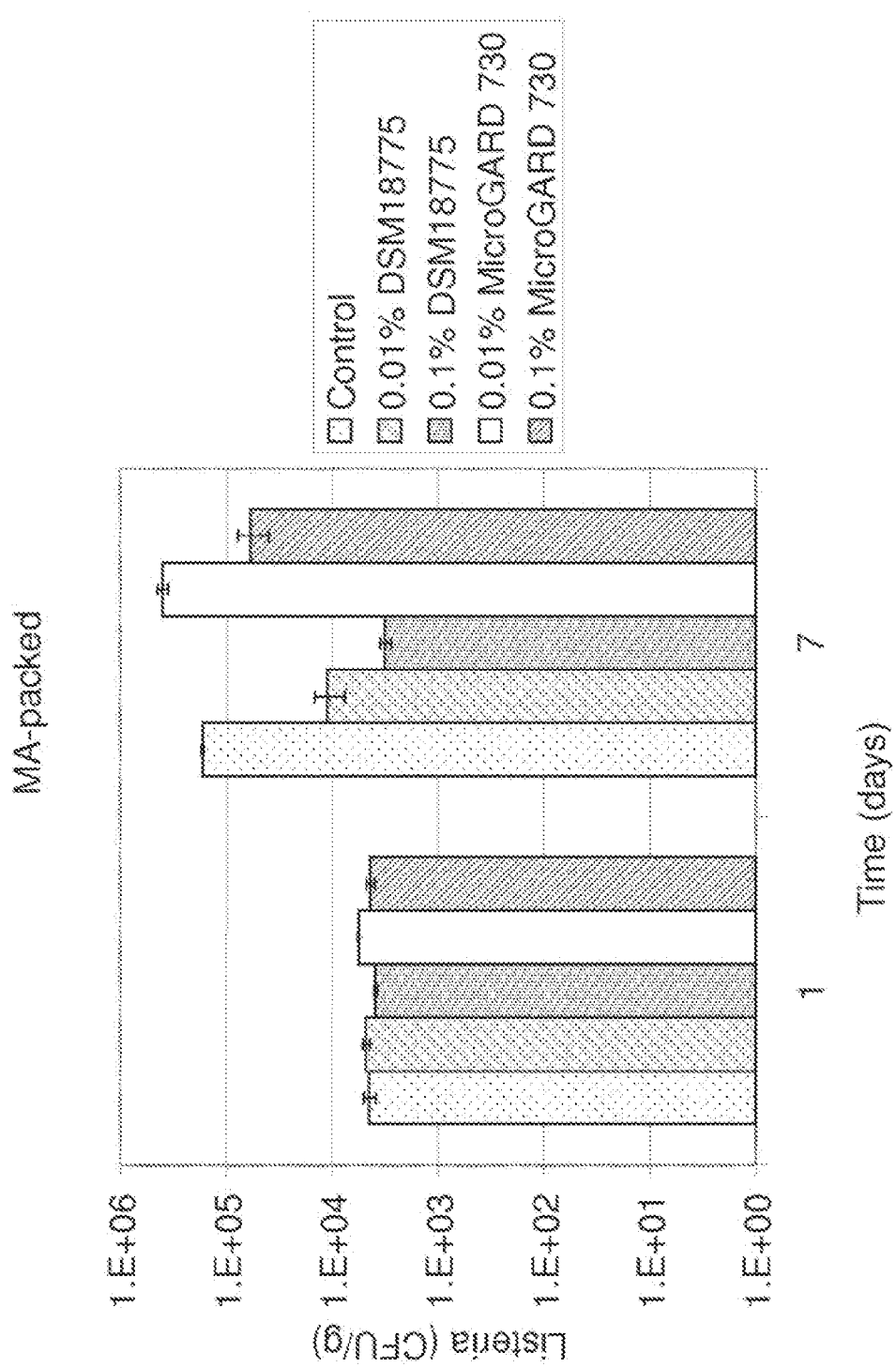
FIG. 7. Cell counts of *L. monocytogenes* exposed to culture eluate of DSM18775 or MicroGARD 730 in different concentrations, as explained in the figure legends to the right, on slices of emulsion sausage stored under Modified Atmosphere (MA, 30% $CO_2$ and 70% $N_2$) 7a, or vacuum (7b) at 7° C. Cell counts were based on determinations made on two different slices of meat, and the bars indicate the standard deviations between these duplicate determinations.

The results of the cell counts are presented in FIG. 7 showing a superior ability of DSM18775 eluate to inhibit growth of Listeria monocytogenes under both packaging conditions. MicroGARD 730 only had a slight growth inhibitory effect at the highest concentration (0.1%) and under MA-conditions. Culture eluate of DSM18775, on the contrary, was able to prevent growth of Listeria monocytogenes at the high concentration of 0.1% under MA-packaging and almost prevented growth under vacuum.

Sensory evaluations showed no effect of either DSM18775 or MicroGARD on the color or the taste of emulsion sausage when MA- or vacuum packed. However, the sensory panel noted a slightly acidic odor of the vacuum-packed emulsion sausage slices with added MicroGARD 730.

Regarding Deposited Microbial Organisms [EXPERT SOLUTION, Rule 13 bis.6 (PCT)]

For all deposited microbial organisms mentioned in the present patent application the following applies.

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

In particular it is requested, that regarding:
Europe

In respect to those designations in which a European Patent is sought a sample or the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

Canada

The applicant requests that, until either a Canadian patent has been issued on the basis of an application or the application has been refused, or is abandoned and no longer subject to reinstatement, or is withdrawn, the Commissioner of Patents only authorizes the furnishing of a sample of the deposited biological material referred to in the application to an independent expert nominated by the Commissioner, the applicant must, by a written statement, inform the International Bureau accordingly before completion of technical preparations for publication of the international application.

Australia

The applicant hereby gives notice that the furnishing of a sample of a microorganism shall only be affected prior to the grant of a patent, or prior to the lapsing, refusal or withdrawal of the application, to a person who is a skilled addressee without an interest in the invention.

Singapore

The applicant hereby requests that the furnishing of a sample of a microorganism shall only be made available to an expert.

The invention claimed is:

1. A process for preparing a composition capable of inhibiting the growth of at least one food-borne pathogenic bacterium said process comprising:
   (a) culturing cells of *Lactobacillus curvatus* deposited in the Deutsche Sammlung von Mikroorganismen and Zellkulturen GmbH under accession number DSM 18775 in a culture medium to produce a bacteriocin that has inhibitory activity against the at least one food-borne pathogenic bacterium; and
   (b) separating a supernatant comprising the bacteriocin from the cultured cells to obtain a composition comprising the bacteriocin.

2. The process according to claim 1, which further comprising subjecting the composition to a drying step to obtain a dried product comprising the bacteriocin.

3. The process according to claim 2, wherein the drying step is freeze drying or spray drying.

4. The process according to claim 1, wherein effective amounts of the composition have a bacteriocidal effect on the at least one food-borne pathogenic bacterium.

5. The process according to claim 1 wherein the at least one food-borne pathogenic bacterium is *Listeria monocytogenes*.

* * * * *